United States Patent [19]
Bowen

[11] Patent Number: 5,545,197
[45] Date of Patent: Aug. 13, 1996

[54] REUSABLE HEAT OR COLD CHEMICAL THERAPY PACK

[75] Inventor: Michael L. Bowen, Arlington, Tex.

[73] Assignee: Tecnol Medical Products, Inc., Fort Worth, Tex.

[21] Appl. No.: 403,295

[22] Filed: Mar. 14, 1995

[51] Int. Cl.⁶ .................................................. A61F 7/00
[52] U.S. Cl. .......................... 607/108; 607/114; 602/4; 383/901; 126/204
[58] Field of Search .................. 607/114, 108–112; 62/4; 126/263.05–.09, 204; 165/46; 383/901; 206/219–222

[56] References Cited

U.S. PATENT DOCUMENTS

| | | | |
|---|---|---|---|
| 2,898,744 | 8/1959 | Robbins | 62/4 |
| 3,191,392 | 6/1965 | Donnelly | 62/4 |
| 3,429,315 | 2/1969 | McDonald | 62/4 |
| 3,763,622 | 10/1973 | Stanley, Jr. | 53/25 |
| 3,893,834 | 7/1975 | Armstrong | 62/4 |
| 4,077,390 | 3/1978 | Stanley et al. | 126/263 |
| 4,081,256 | 3/1978 | Donnelly | 62/4 |
| 4,427,010 | 1/1984 | Marx | 128/402 |
| 4,462,224 | 7/1984 | Dunshee et al. | 62/530 |
| 4,537,184 | 8/1985 | Williams, Jr. | 128/90 |
| 4,751,119 | 6/1988 | Yukawa | 428/35 |
| 4,780,117 | 10/1988 | Lahey et al. | 62/4 |
| 4,931,333 | 6/1990 | Henry | 428/76 |
| 4,986,076 | 1/1991 | Kirk et al. | 62/4 |
| 5,163,504 | 11/1992 | Resnick | 165/47 |
| 5,184,470 | 2/1993 | Moser et al. | 62/4 |
| 5,205,278 | 4/1993 | Wang | 126/263 |
| 5,261,241 | 11/1993 | Kitahara et al. | 62/4 |
| 5,275,156 | 1/1994 | Milligan et al. | 607/114 |
| 5,466,251 | 11/1995 | Brunson et al. | 607/112 |

*Primary Examiner*—Angela D. Sykes
*Assistant Examiner*—Robert L. Nasser, Jr.
*Attorney, Agent, or Firm*—Baker & Botts, L.L.P.

[57] ABSTRACT

A reusable heat or cold chemical therapy pack (10) is provided that has two pairs of compartments (12a and 14a; 12b and 14b). One pair of compartments (12a, 14a) is located on one side of the pack (10) and the other pair (12b, 14b) is located on the opposite side. Each pair of compartments is separated by a rupturable seam (16a, 16b). Each compartment contains a chemical reactant. One compartment in each pair (12a, 12b) is filled with a liquid reactant, and the other compartment in each pair (14a, 14b) is filled with solid beads (15) of reactant material. The compartments proximate those of the opposite pair contain different reactant materials. Therefore, since the solid reactant material (15) will not transfer pressure to the rupturable seam (16a, 16b), only one side of the pack (10) can be activated at a time by pressing on the respective compartment (12a, 12b) containing the liquid reactant.

14 Claims, 1 Drawing Sheet

REUSABLE HEAT OR COLD CHEMICAL THERAPY PACK

TECHNICAL FIELD OF THE INVENTION

The present invention relates generally to the field of heat or cold therapy devices, and more specifically, to a heat or cold chemical therapy pack that can be used more than once.

BACKGROUND OF THE INVENTION

Cold therapy is an established practice used in the medical profession to treat certain limb injuries, such as, for example, sprained or strained arm or leg muscles, or injuries to joints. Generally, these types of injuries should be chilled to slow blood flow, which reduces swelling, pain, and further damage. A typical course of cold therapy treatment is to apply ice for a specified period to the injured region of the limb. Alternatively, a pack or bag containing a chemical agent that reacts (endothermically) to produce cold may be applied to the injured region.

Heat therapy may be used, in other circumstances, to warm up or limber muscles by increasing blood flow. For example, athletes may apply heat with a hot water bag for a specified period to thighs or calf muscles prior to an event. Alternatively, a pack or bag containing a chemical agent that reacts (exothermically) to produce heat may be applied to the region of interest.

A number of devices that use endothermic or exothermic reactions for cooling or heating body parts are known. For example, U.S. Pat. No. 4,986,076 to Kirk et al. and U.S. Pat. No. 2,898,744 to Robbins both disclose a flexible, plastic cooling bag sealed along its edges. The cooling bag is separated by a frangible barrier into two portions: a freezing chemical mixture (salt) portion and a liquid (water) portion. A cooling reaction is activated by squeezing or applying pressure to the bag, which ruptures the frangible barrier and thus allows the salt and liquid portions to mix. The resulting chemical mixture causes an endothermic reaction, which produces a cooling effect. The cooled bag is applied to a body part. However, once the chemical reaction is exhausted, the chemical mixture cannot be reactivated, and the cooling bag is thus not reusable. Moreover, separate bags are used for cooling and heating.

A reusable hot or cold pack is disclosed in U.S. Pat. No. 4,462,224 to Dunshee et al. A flexible pack, made from a polyester film material, is separated into three compartments. The adjacent compartments are separated by predictably rupturable seams. Two adjacent compartments contain either endothermic or exothermic reactant components. For example, one of those adjacent compartments contains a solvent composed primarily of water. The second compartment contains a water soluble, exothermic or endothermic solute. The third compartment, which is adjacent to the second compartment, contains a gelling agent. The endothermic or exothermic reaction is activated by pulling apart or jerking at the sides of the pack to rupture the seam between the first two compartments. After the chemical reaction is exhausted, the seam between the second and third compartments is ruptured. The gelling agent thus mixes with the already combined contents of the other compartments. The resulting gelled material can then be cooled in a refrigerator, and as such, the pack is reusable. However, the use of a gelled material requires access to a refrigerator to create the cooling effect, which is a very inconvenient process.

Accordingly, a need has arisen for a hot or cold chemical therapy device that is reusable but still convenient to use. A need also exists for a single, reusable device that can provide both heat and cold chemical therapy.

SUMMARY OF THE INVENTION

In accordance with a preferred embodiment of the present invention, a reusable heat or cold chemical therapy pack is provided that has two pairs of compartments. One pair of compartments is located on one side of the pack and the other pair is located on the opposite side. Each pair of compartments is separated by a rupturable seam. Each compartment contains a chemical reactant. One compartment in each pair is filled with a liquid reactant, and the other compartment in each pair is filled with solid beads of reactant material. The compartments proximate those of the opposite pair contain different reactant materials. Therefore, since the solid reactant material will not transfer pressure to the rupturable seam, only one side of the pack can be activated at a time by pressing on the respective compartment containing the liquid reactant.

An important technical advantage of the invention is that it can be used more than once, which makes the pack more convenient to use and less costly for the user. A second important technical advantage of the invention is that one pack can be used both for heat and cold therapy, which increases the versatility of the pack while reducing its cost to the user.

DETAILED DESCRIPTION OF THE INVENTION

Figure 1:
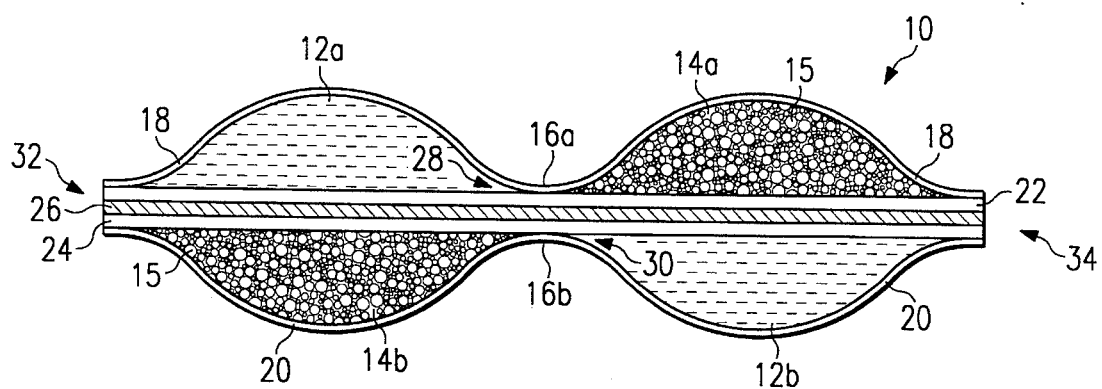
FIG. 1 is a side view of a hot or cold chemical therapy pack according to preferred embodiment of the present invention.
Figure 2:
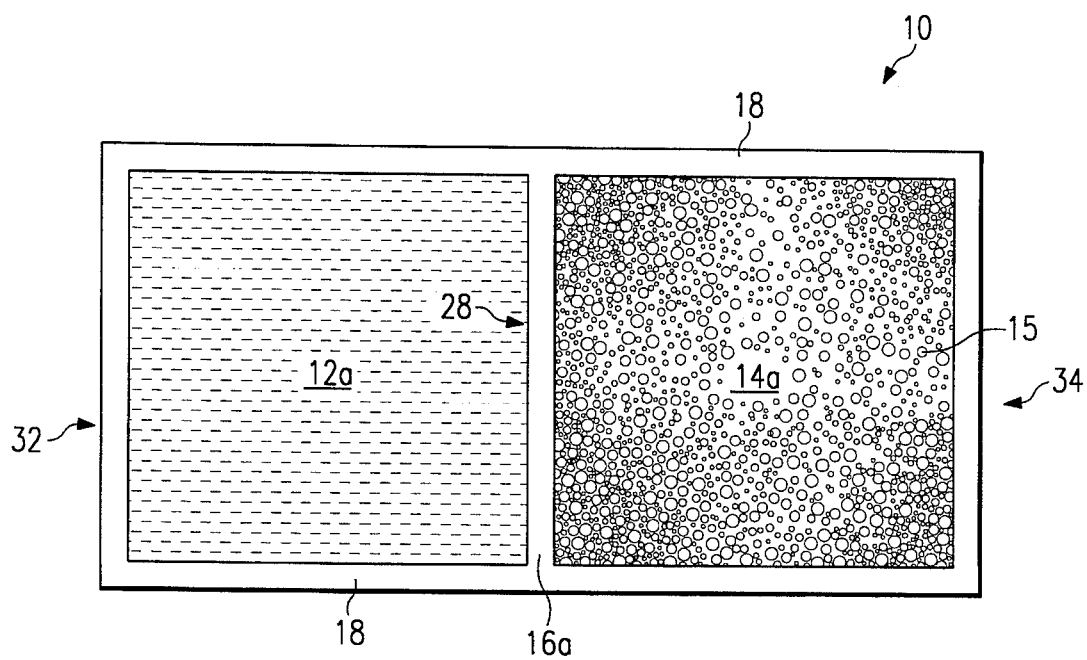
FIG. 2 is a top view of the hot or cold chemical therapy pack shown in FIG. 1.
Figure 3:
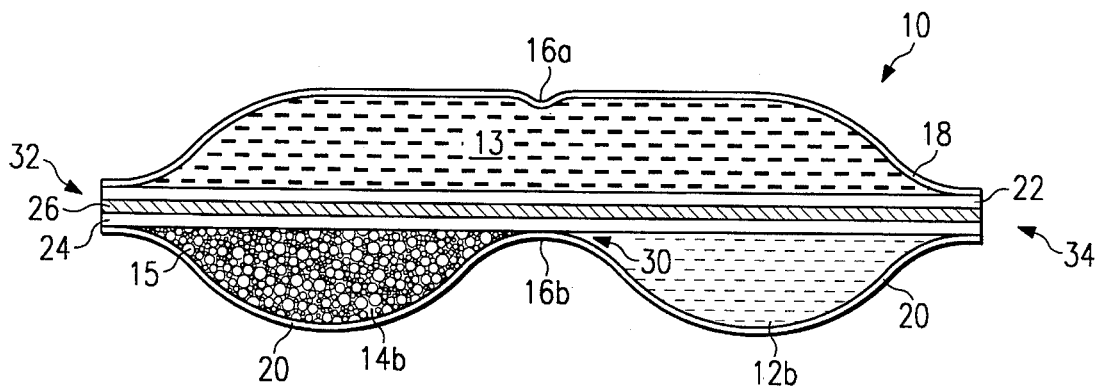
FIG. 3 is a side view of the hot or cold chemical therapy pack shown in FIG. 1 during an initial activation.

The preferred embodiment of the present invention and its advantages are best understood by referring to FIGS. 1–3 of the drawings, like numerals being used for like and corresponding parts of the various drawings.

FIG. 1 illustrates a side view of a hot or cold chemical therapy pack 10 structured in accordance with a preferred embodiment of the present invention. Pack 10 may be applied to a human or animal body part, or even used for other hot or cold applications, such as, for example, heating or cooling drinks and foodstuffs. Pack 10 is constructed with a pair of rectangular sheets 18 and 20 of a relatively flexible, plastic or vinyl film material. For example, sheets 18 and 20 can be a film of material made of polyethylene, polypropylene or polyvinylchloride. However, the material composition of sheets 18 and 20 is not intended to act as a limitation on the scope of the present invention. Essentially, sheets 18 and 20 can be made of any one of a number of relatively strong, but pliable materials known and used in the heat or cold therapy art. Three additional rectangular sheets 22, 24 and 26 essentially forming a "sandwich" are arranged between sheets 18 and 20. Preferably, sheets 22 and 24 are constructed from the same material used for sheets 18 and 20. Sheet 26 may be made from a material that has heat or cold insulating properties, such as, for example, a layer of foam material. Sheet 26 may also be constructed from the same material used for sheets 18 and 20, for applications where the material's insulating properties are relatively unimportant. In addition, although insulating layer 26 is shown in FIG. 1 arranged between sheets 22 and 24, the invention is not intended to be so limited. For example, sheets 22 and 24 can be excluded for design reasons. Generally, the insulating function of sheet 26 is provided, if so desired, to ensure that the cold or heat generated by pack 10 is directed substantially toward the body part or other item to be cooled or heated by pack 10. For example, upon activation, heat or cold will be directed substantially normal to the upper or lower surface of sheet 26, depending on which portion of pack 10 has been activated.

FIG. 2 is a top view of the heat or cold chemical therapy pack 10 shown in FIG. 1. Referring now to FIGS. 1 and 2, sheets 18, 20, 22, 24 and 26 are sealed to each other, along their peripheries, by a relatively strong heat seal. Although heat sealing of these sheets is preferable, any method of mechanically sealing sheets 18, 20, 22, 24 and 26 along their peripheries can be used, such as, for example, an RF seal, ultrasonic seal, glue, etc. Pack 10 is separated into four compartments 12a, 12b, 14a and 14b by seams 16a and 16b and sheets 22, 24 and 26. Seams 16a and 16b are comparatively weaker seals than the peripheral seal of sheets 18, 20, 22, 24 and 26. Consequently, seams 16a and 16b can be ruptured with predictable pressure without rupturing the above-described peripheral seals.

Compartment 12a of pack 10 is filled with a liquid reactant (e.g., a solvent) composed primarily of water. A salt or other appropriate chemical can be added to the liquid solvent to lower the freezing point of the water, in order to keep the water from freezing prior to activation. The liquid reactant can also be one of a number of known liquid reactants such as, for example, a mixture of water and aqueous ammonia. For an endothermic reaction (cooling), compartment 14a is filled with a plurality of water soluble, spherically shaped beads 15 that are capable of being dissolved in the water, preferably beads of ammonium nitrate. Alternatively, for an exothermic reaction (heating), the water soluble, spherically shaped beads in compartment 14a can be made of calcium chloride. Such spherical, soluble beads are referred to as "prills" in the chemical therapy pack art. Pack 10 preferably contains "prills" or some structural and chemical equivalent of "prills." For example, these water soluble beads 15 could be very small particles arranged to form a virtually incompressible "slurry." Examples of materials that can be used for exothermal reactants include quick lime, sodium hydroxide, cobalt, chromium, iron, iron hydroxide, magnesium, manganese, molybdenum, tin oxide(II), titanium, sodium, calcium hydroxide, metallic sodium, magnesium chloride and anhydrous calcium chloride ($CaCl_2$). Examples of materials that can be used for endothermal reactions include ammonium nitrate ($NH_4NO_3$), and salts such as ammonium sulfurate, potassium nitrate and sodium thiosulfate.

Compartment 12b is also filled with the same liquid reactant used in compartment 12a. Also, compartment 14b is filled with water soluble, exothermic or endothermic "prills." Essentially, compartments 12a and 14a are arranged in a reverse mirror image to that of compartments 12b and 14b. Preferably, compartments 14a and 14b both contain either endothermic "prills" for cooling, or exothermic "prills" for heating applications. However, if separate endothermic and exothermic reactions are desired with a single pack 10, then one of compartments 14a or 14b can be filled with the endothermic "prills," while the other of compartments 14a or 14b can be filled with the exothermic "prills."

Although pack 10 is shown in FIG. 2 as rectangularly shaped, the invention is not intended to be limited to any particular shape or dimension, so pack 10 can be any practical size or shape. For example, pack 10 can be oval-shaped, substantially circular in shape, or substantially rectangular in shape with rounded corners.

In order to activate pack 10 for use, seam 16a or 16b is ruptured by applying pressure to, squeezing, or kneading either of respective compartments 12a or 12b. For example, if external pressure is applied to compartment 12a, the pressure is transferred to seal 16a in the direction of the arrow denoted as 28. Once a predetermined amount of pressure is reached at seal 16a, the seal ruptures and the contents of compartments 12a and 14a are merged and thus mix together to react. Consequently, the desired endothermic or exothermic reaction is activated and the upper portion of pack 10 creates either a cooling or heating effect. Because of the insulating effect of sheet 26, the resulting cooling or heating effect of the reaction is felt in the upward direction in FIG. 1. So, the upper portion of pack 10 can be placed against the body part or item to be cooled or heated. Typically, pack 10 will cool or heat a surface for up to 30 minutes per activation. Once the chemical reaction between the mixed contents of compartments 12a and 14a is exhausted, pack 10 can be flipped over and reused. Specifically, external pressure is then applied to compartment 12b. This pressure is transferred to seal 16b in the direction of the arrow denoted as 30. Consequently, at a predetermined amount of pressure, seal 16b is ruptured and the contents of compartments 12b and 14b are mixed to activate a desired cooling or heating reaction for a second time.

It is an important aspect of the invention that compartments 14a and 14b are filled with "prills" or solid reactant material with sufficient density to be virtually incompressible. Therefore, any pressure exerted against compartments 14a or 14b will not be transferred by the "prills" to respective seal 16a or 16b and cause that seal to rupture prematurely.

FIG. 3 is a side view of the multiple use heat or cold chemical therapy pack 10 shown in FIGS. 1 and 2, which illustrates one use or single activation of pack 10. With seal 16a ruptured, former compartments 12a and 14a are reformed into one compartment 13. The reactants that were formerly contained in compartments 12a and 14a are mixed in compartment 13, which provides the desired cooling or heating reaction. However, seal 16b is still intact. Consequently, as shown in FIG. 3, the reactants in compartments 12b and 14b are still available to provide a second cooling or heating reaction. Therefore, the present heat or cold chemical therapy pack 10 is reusable.

Although the present invention and its advantages have been described in detail, it should be understood that various changes, substitutions and alterations can be made therein without departing from the spirit and scope of the invention as defined by the appended claims.

What is claimed is:

1. A reusable heat or cold chemical therapy pack, comprising:

a first compartment containing a first reactant;

a second compartment containing a second reactant, said first and second compartments separated by a predictably rupturable first barrier, said first and second compartments located on a top of said pack;

a third compartment containing a third reactant; and a fourth compartment containing a fourth reactant, said third and fourth compartments separated by a predictably rupturable second barrier, said third and fourth compartments located on a bottom side of said pack said first and second reactants reacting exothermically or endothermically upon contact and said third and fourth reactants reacting exothermically or endothermically upon contact.

2. The reusable heat or cold chemical therapy pack according to claim 1, wherein said first and second reactants react endothermically upon contact.

3. The reusable heat or cold chemical therapy pack according to claim 2, wherein said third and fourth reactants react endothermically upon contact.

4. The reusable heat or cold chemical therapy pack according to claim 1, wherein said first and second compartments are separated from said third and fourth compartments by a first layer of material.

5. The reusable heat or cold chemical therapy pack according to claim 4, wherein said first layer of material further comprises an insulating layer of material.

6. The reusable heat or cold chemical therapy pack according to claim 1, wherein said second and third reactants comprise arrangements of an incompressible material.

7. The reusable heat or cold chemical therapy pack according to claim 1, wherein said second and third reactants comprise a plurality of prills.

8. The reusable heat or cold chemical therapy pack according to claim 1, wherein said second and third reactants comprise a plurality of solid reactant beads.

9. The reusable heat or cold chemical therapy pack according to claim 1, wherein a portion of said third compartment is disposed below a portion of said first compartment and wherein a portion of said fourth compartment is disposed below a portion of said second compartment.

10. A reusable heat or cold chemical therapy pack, comprising:

a first compartment containing a first reactant;

a second compartment containing a second reactant, said first and second compartments separated by a predictably rupturable first barrier, said first and second compartments proximate to only a first side of said pack;

a third compartment containing a third reactant;

a fourth compartment containing a fourth reactant, said third and fourth compartments separated by a predictably rupturable second barrier, said third and fourth compartments proximate to only a second side of said pack;

wherein said first and second reactants react endothermically upon contact; and wherein said third and fourth reactants react exothermically upon contact.

11. A reusable heat or cold chemical therapy pack, comprising:

a first sheet of a generally rectangularly-shaped material;

a second sheet of a generally rectangularly-shaped material disposed below said first sheet;

a third sheet of a generally rectangularly-shaped material disposed below said second sheet, each sheet bounded by an edge, wherein said sheets are peripherally sealed together proximate to the edges to define a first generally rectangularly-shaped sealed pack between said first and second sheets and a second generally rectangularly-shaped sealed pack between said second and third sheets;

a first rupturable seam within said first sealed pack, said first seam extending across said first sealed pack to define a first and second compartment therein;

a second rupturable seam within said second sealed pack, said second seam extending across said second sealed pack to define a third and fourth compartment therein;

a first reactant contained in said first compartment;

a second reactant contained in said second compartment;

a third reactant contained in said third compartment;

a fourth reactant contained in said fourth compartment, said first and second reactants reacting exothermically or endothermically upon contact and said third and fourth reactants reacting exothermically or endothermically on contact, said second and third reactants comprising an incompressible material.

12. The reusable heat or cold chemical therapy pack according to claim 11, wherein said second sheet comprises an insulating layer of material.

13. The reusable heat or cold chemical therapy pack according to claim 11, wherein said peripherally sealed edge surfaces are heat sealed.

14. The reusable heat or cold chemical therapy pack according to to claim 11 wherein said second sheet comprises a plurality of generally rectangularly-shaped layers of material.

* * * * *